United States Patent [19]
Fodor et al.

[11] Patent Number: 5,541,061
[45] Date of Patent: Jul. 30, 1996

[54] METHODS FOR SCREENING FACTORIAL CHEMICAL LIBRARIES

[75] Inventors: Stephen P. A. Fodor, Palo Alto; Lubert Stryer, Stanford, both of Calif.

[73] Assignee: Affymax Technologies N.V., Curacao, Netherlands Antilles

[21] Appl. No.: 876,792

[22] Filed: Apr. 29, 1992

[51] Int. Cl.$^6$ .................. G01N 33/53; G01N 33/545
[52] U.S. Cl. .................. 435/6; 435/5; 435/7.1; 436/501; 436/518; 530/333; 530/334
[58] Field of Search .................. 435/5, 7.1, 6; 436/501, 436/518; 550/333, 334

[56] References Cited

U.S. PATENT DOCUMENTS

| | | | |
|---|---|---|---|
| 4,689,405 | 8/1987 | Frank et al. | 536/27 |
| 4,979,824 | 12/1990 | Mathies et al. | 356/318 |
| 5,143,854 | 9/1992 | Pirrung et al. | 436/518 |

FOREIGN PATENT DOCUMENTS

| | | | |
|---|---|---|---|
| 8600991 | 2/1986 | WIPO | |
| WO90/15070 | 12/1990 | WIPO | C07K 1/04 |
| WO92/09300 | 6/1992 | WIPO | A61K 37/02 |

OTHER PUBLICATIONS

Pinilla et al., "Rapid Identification of High Affinity Peptide Ligands Using Positional Scanning Synthetic Peptide Combinatorial Libraries," *BioTechniques* (1992) 13:901–905.
Houghten et al., *Nature* (1991) 354:84–86.
Furka et al., *Int. J. Peptide Protein Res.* (1991) 37:487–493.
Furka et al., Abstract from *14th Int'l Congress of Biochem.*, Prague, Czechoslovakia, Jul. 10–15, 1988.
Furka et al., Abstract from *Xth Int'l Symposium on Medicinal Chemistry*, Budapest, Hungary, Aug. 15–19, 1988.
Lam et al., *Nature* (1991) 354:82–84.
Fodor et al., *Science* (1991) 251:767–777.
USSN 762,522, filed Sep. 18, 1991, entitled "Method Of Synthesizing Diverse Collections Of Oligomers".
Gait, *Oligonucleotide Synthesis*, Chapters 3 and 4, IRL Press, 1990.
Atherton et al., *Solid Phase Peptide Synthesis*, Chapters 2 and 3, IRL Press, 1989.
Frank et al., "Facile and rapid 'spot-synthesis' of large numbers of peptides on membrane sheets," *Peptides 1990, Proceedings of the Twenty-First European Peptide Symposium*, ESCOM Science Publishers B.V., 1991, pp. 151–152.
Frank et al., "Simultaneous Multiple Peptide Synthesis Under Continuous Flow Conditions on Cellulose Paper Discs as Segmental Solid Supports," *Tetrahedron* (1988) 44:6031–6040.
Frank et al., "A new general approach for the simultaneous chemical synthesis of large numbers of oligonucleotides: segmental solid supports," *Nucleic Acids Research* (1983) 11:4365–4377.

*Primary Examiner*—Margaret Parr
*Assistant Examiner*—Lora M. Green
*Attorney, Agent, or Firm*—Townsend and Townsend and Crew

[57] ABSTRACT

A method and library for determining the sequence of monomers in a polymer which is complementary to a receptor. The method provides for formation of pooled (6) and separate (10, 12) products. Separate products are subjected only to subsequent pooled coupling steps. Each pooled product is subsequently divided for formation of pooled and separate products. The resulting polymer library includes groups of polymer products. A first group of products (42) is used to identify the monomer at a first location in a polymer that is complementary to a receptor. A second group of products (44) is used to identify the monomer at a second location in a polymer that is complementary to a receptor.

8 Claims, 8 Drawing Sheets

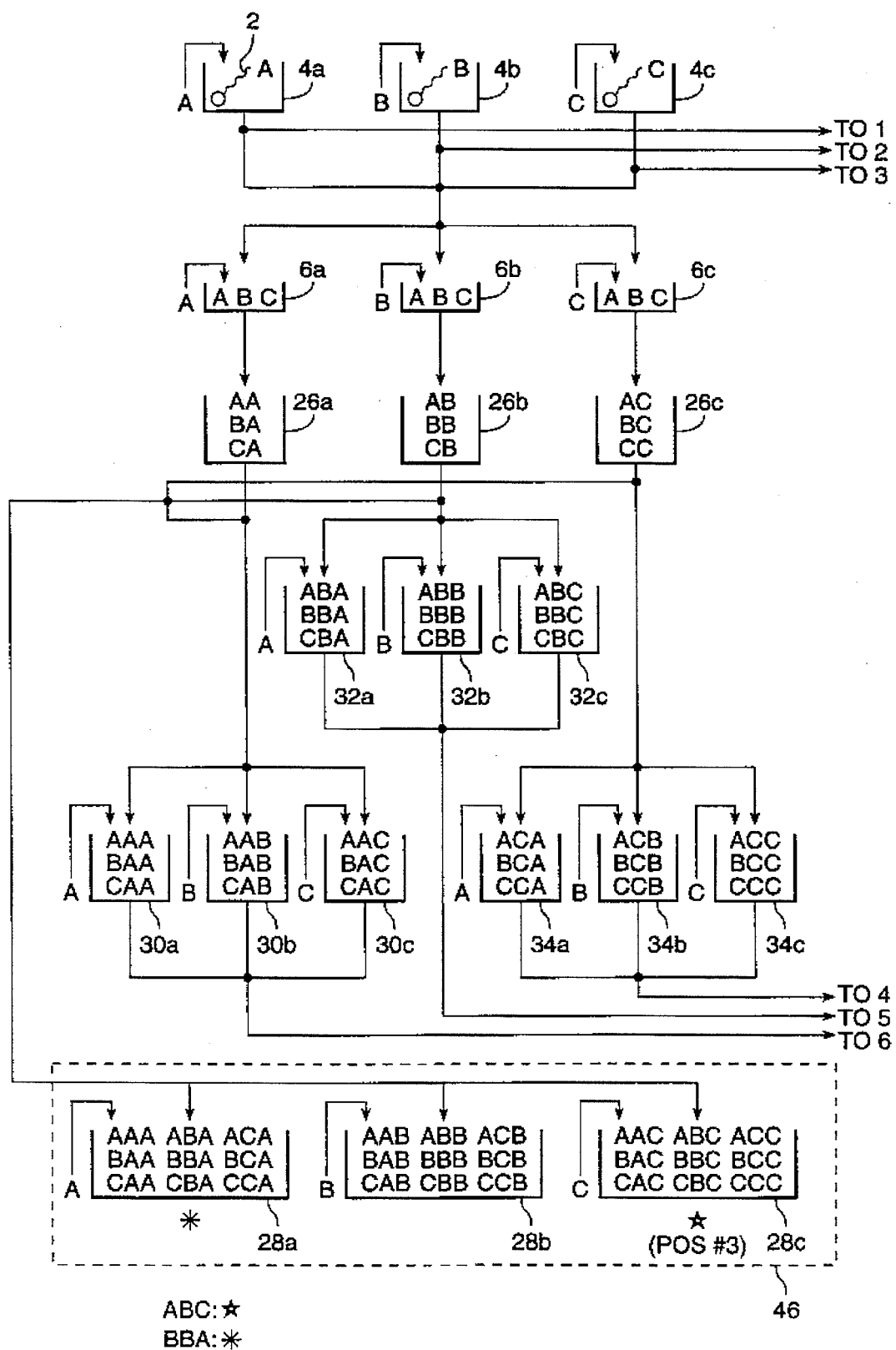
FIG. 1b.1

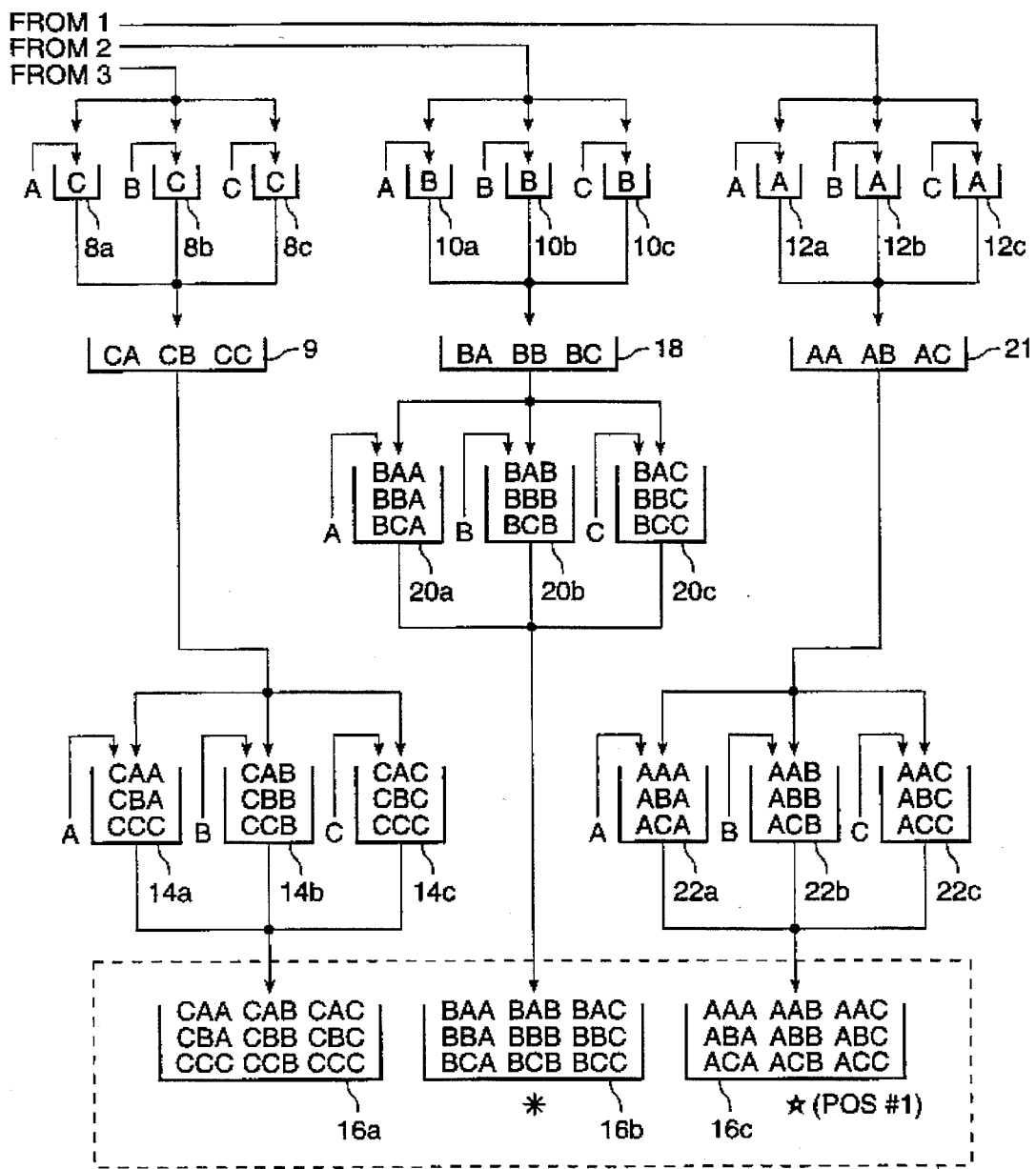
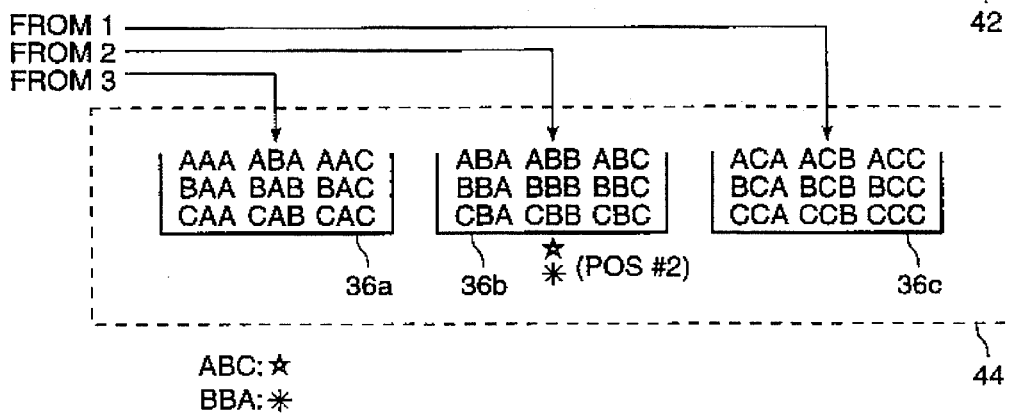
FIG. 1b.2

METHODS FOR SCREENING FACTORIAL CHEMICAL LIBRARIES

BACKGROUND OF THE INVENTION

The present invention relates to the field of polymer screening. More specifically, in one embodiment the invention provides an improved polymer library and method of using the library to identify a polymer sequence that is complementary to a receptor.

Many assays are available for measuring the binding affinity of receptors and ligands, but the information which can be gained from such experiments is often limited by the number and type of ligands which are available. Small peptides are an exemplary system for exploring the relationship between structure and function in biology. When the twenty naturally occurring amino acids are condensed into peptides they form a wide variety of three-dimensional configurations, each resulting from a particular amino acid sequence and solvent condition. The number of possible pentapeptides of the 20 naturally occurring amino acids, for example, is $20^5$ or 3.2 million different peptides. The likelihood that molecules of this size might be useful in receptor-binding studies is supported by epitope analysis studies showing that some antibodies recognize sequences as short as a few amino acids with high specificity.

Prior methods of preparing large numbers of different oligomers have been painstakingly slow when used at a scale sufficient to permit effective rational or random screening. For example, the "Merrifield" method, described in Atherton et al., "Solid Phase Peptide Synthesis," IRL Press, (1989), incorporated herein by reference for all purposes, has been used to synthesize peptides oil a solid support such as pins or rods. The peptides are then screened to determine if they are complementary to a receptor. Using the Merrifield method, it is not economically practical to screen more than a few peptides in a day.

Similar problems are encountered in the screening of other polymers having a diverse basis set of monomers. For example, various methods of oligonucleotide synthesis such as the phosphite-triester method and the phosphotrieseter method, described in Gait, "Oligonucleotide Synthesis," IRL Press, (1990), incorporated herein by reference for all purposes, have similar limitations when it is desired to synthesize many diverse oligonucleotides for screening.

To screen a larger number of polymer sequences, more advanced techniques have been disclosed. For example, Pirrung et al., WO 90/15070, incorporated herein by reference for all purposes, describes a method of synthesizing a large number of polymer sequences on a solid substrate using light directed methods. Dower et al., U.S. application Ser. No. 07/762,522, also incorporated by reference herein for all purposes, describes a method of synthesizing a library of polymers and a method of use thereof. The polymers are synthesized on beads, for example. A first monomer is attached to a pool of beads. Thereafter, the pool of beads is divided, and a second monomer is attached. The process is repeated until a desired, diverse set of polymers is synthesized.

Other methods of synthesizing and screening polymers have also been proposed. For example, Houghten et al., "Generation and Use of Synthetic Peptide Combinatorial Libraries for Basic Research and Drug Discovery," *Nature* (1991) 354:84–86, discuss a method of generating peptide libraries that are used for screening the peptides for biological activity. Houghten synthesized a peptide combinatorial library (SPCL) composed of some $34 \times 10^6$ hexapeptides and screened it to identify antigenic determinants that are recognized by a monoclonal antibody. Furka et al., "General Method for Rapid Synthesis of Multicomponent Peptide Mixtures," *Int. J. Peptide Protein Res.* (1991) 37:487–493, discusses a method of synthesizing multicomponent peptide mixtures. Furka proposed pooling as a general method for the rapid synthesis of multicomponent peptide mixtures and illustrated its application by synthesizing a mixture of 27 tetrapeptides and 180 pentapeptides. Lam et al., "A new type of synthetic peptide library for identifying ligand-binding activity," *Nature* (1991) 354:82–84 used pooling to generate a pentapeptide bead library that was screened for binding to a monoclonal antibody.

Lam's synthetic peptide library consists of a large number of beads, each bead containing peptide molecules of one kind. Beads that bind a target (e.g., an antibody or strepavidin) are rendered colored or fluorescent. Lam reports that several million beads distributed in 10–15 petri dishes can be screened with a low-power dissecting microscope in an afternoon. Positive beads are washed with 8M guanidine hydrochloride to remove the target protein and then sequenced. The 100–200 μm diameter beads contain 50–200 pmol of peptide, putatively well above their 5 pmol sensitivity limit. Three pentapeptide beads were sequenced daily. The essence of Lam's method is that the identity of positive beads is established by direct sequencing.

Houghten et al. use a different approach to identify peptide sequences that are recognized by an antibody. Using the nomenclature described herein, Houghten et al. screened an $X_6X_5X_{4p}X_{3p}X_{2p}X_{1p}$ library and found that the mixture $DVX_{4p}X_{3p}X_{2p}X_{1p}$ had greatest potency in their inhibition assay. Houghten then synthesized a $DVX_4X_{3p}X_{2p}X_{1p}$ library and identified the most potent amino acid in the third position. After three more iterations, they found that DVPDYA (SEQ ID NO:1) binds to the antibody with a $K_d$ of 30 nM. The essence of Houghten's method is recursive retrosynthesis, in which the number of pooled positions decreases by one each iteration.

While meeting with some success, prior methods have also met with certain limitations. For example, it is sometimes desirable to avoid the use of the equipment necessary to conduct light directed techniques. Also, some prior methods have not produced the desired amount of diversity as efficiently as would be desired.

From the above, it is seen that an improved method and apparatus for synthesizing a diverse collection of chemical sequences is desired.

SUMMARY OF THE INVENTION

An improved polymer library and method of screening diverse polymers is disclosed. The system produces libraries of polymers in an efficient manner, and utilizes the libraries for identification of the monomer sequence of polymers which exhibit significant binding to a ligand.

According to one aspect of the invention, a library of polymers is formed using "pooled" and "unpooled" (or "separate") coupling steps. In the pooled steps, each of the monomers from a basis set of monomers is coupled to the terminus of a growing chain of monomers on a plurality of previously mixed solid substrates. The mixed substrates are divided for coupling of each individual monomer in a basis set. In separate steps, the substrates are not intermixed from a previous coupling step, and each of the monomers in a basis set is separately coupled to the terminus of a growing chain of monomers on a plurality of the unmixed substrates.

According to one preferred aspect of the invention, pooled steps and unpooled steps are ordered such that the identification of a monomer sequence which binds to a receptor can be readily identified from the library. For example, according to one preferred embodiment of the invention, several groups of products are derived from the synthesis steps. Each group is used to identify the monomer at a specific position in the polymer chain.

According to most preferred aspects of the invention, the library is constructed using an ordered series of coupling steps in which products resulting from a separate step are, thereafter, only subjected to pooled coupling steps. Products resulting from a pooled coupling step which have not been previously subjected to an unpooled step are always divided for pooled and unpooled coupling. This ordered series of steps results in a relatively small number of coupling steps, but still allows for identification of the monomer sequence of a polymer which is complementary to a receptor of interest. For example, a first group of products is used to identify the monomer at a first location in a polymer that is complementry to a receptor. A second group of products is used to identify the monomer at a second location in a polymer that is complementary to a receptor.

Accordingly, in one embodiment of the invention provides a polymer library screening kit. The kit includes families of polymers $X_3$—$X_{2p}$—$X_{1p}$, $X_{3p}$—$X_2$—$X_{1p}$, and $X_{3p}$—$X_{2p}$—$X_1$ wherein $X_{3p}$—$X_{2p}$—$X_1$ comprises a collection of at least first and second polymer mixtures, the first polymer mixture having a first monomer in a first position of polymer molecules therein, and different monomers in second and third positions of the polymer molecules therein, and wherein the second polymer mixture has a second monomer in the first position of polymer molecules therein, and different monomers in second and third positions of the polymer molecules therein; $X_{3p}$—$X_2$—$X_{1p}$ comprises a collection of at least third and fourth polymer mixtures, the third polymer mixture having a third monomer in the second position and the fourth polymer mixture having a fourth monomer in the second position, each of the third and fourth polymer mixtures having different monomers in the first and third positions; and $X_3$—$X_{2p}$—$X_{1p}$ comprises a collection of at least fifth and sixth polymer mixtures, the fifth polymer mixture having a fifth monomer in the third position and the sixth polymer mixture having a sixth monomer in the third position, each of the fifth and sixth polymer mixtures having different monomers in the first and second positions, wherein the first, third, and fourth monomers are the same or different and the second, fourth, and fifth monomers are the same or different.

A method of identifying first and second monomers in a polymer that is complementary to a receptor is also provided. The method includes the steps of coupling first and second monomers in a first basis set to individual substrates and mixing substrates to form first pooled products; coupling the first and second monomers from the first basis set to individual substrates, and not mixing the substrates to form at least first and second separate products; separately coupling first and second monomers from a second basis set to substrates from the first pooled products and not mixing the substrates to form at least third and fourth separate products, the second basis set being the same or different than the first basis set; coupling the first and second monomers from the second basis set to individual substrates from the first separate products and mixing the substrates to form second pooled products; coupling the first and second monomers from the second basis set to individual substrates from the second separate products to form third pooled products; and exposing a receptor to the third and fourth separate products to identify a second monomer in a polymer which is complementary to a receptor, and exposing the second and third pooled products to the receptor to identify a first monomer in a polymer which is complementary to a receptor.

A polymer screening technique using factoring is also disclosed.

A further understanding of the nature and advantages of the inventions herein may be realized by reference to the remaining portions of the specification and the attached drawings.

BRIEF DESCRIPTION OF THE DRAWINGS

FIGS. 1a and 1b are schematic diagrams of specific embodiments of the invention;

DESCRIPTION OF THE PREFERRED EMBODIMENTS

CONTENTS

Figure 1A:
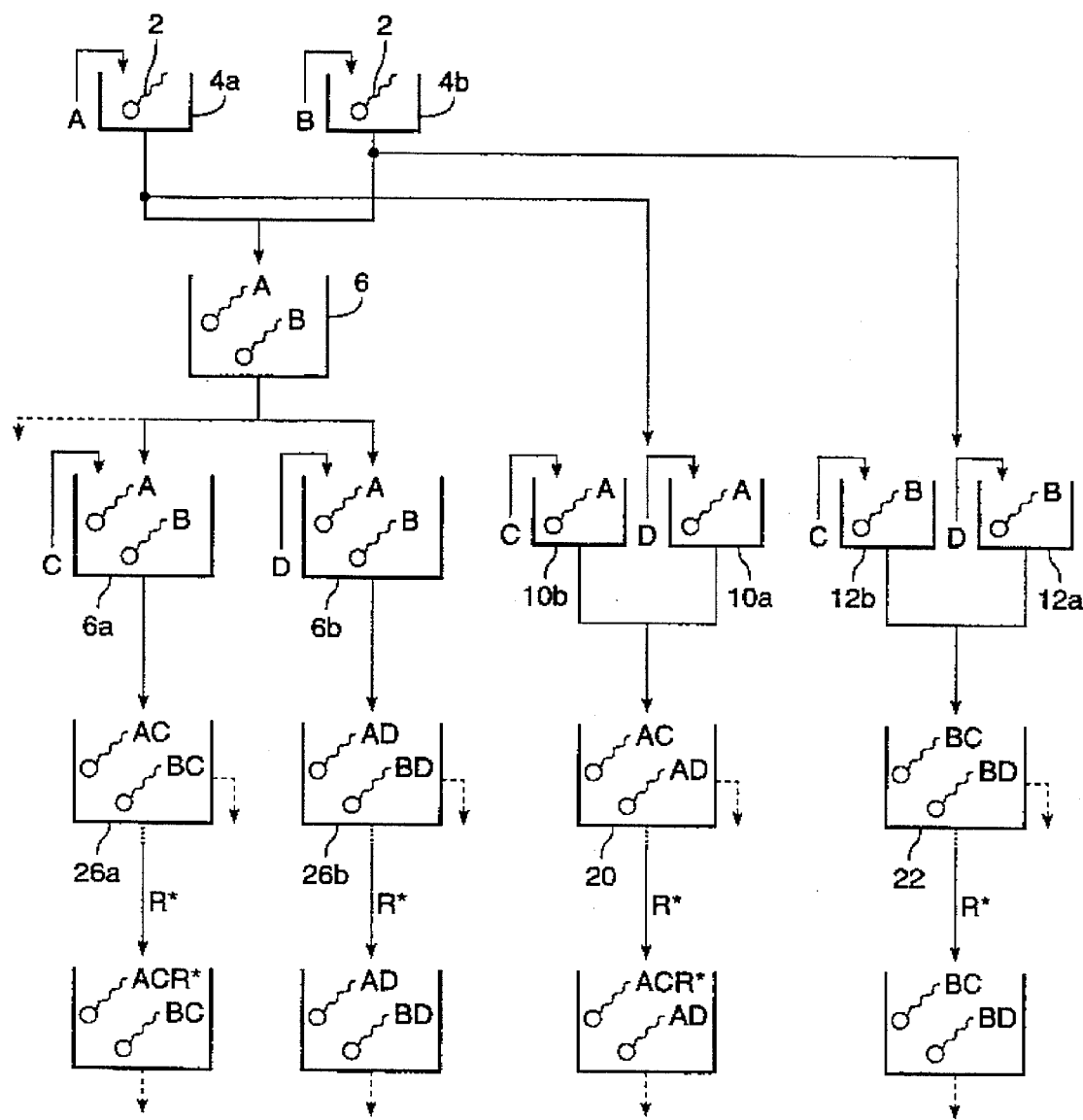

I. Terminology
II. Overall Description
III. Polynomial Factoring Applied to Screening
IV. Conclusion
I. Terminology Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones (e.g., opiates, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Monomer: A member of the set of small molecules which are or can be joined together to form a polymer. The set of monomers includes but is not restricted to, for example, the set of common L-amino acids, the set of D-amino acids, the set of synthetic and/or natural amino acids, the set of nucleotides and the set of pentoses and hexoses, as well as subsets thereof. The particular ordering of monomers within a polymer is referred to herein as the "sequence" of the polymer. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members which are modified after synthesis. The invention is described herein primarily with regard to the preparation of molecules containing sequences of monomers such as amino acids, but could readily be applied in the preparation of other polymers. Such polymers include, for example, both linear and cyclic polymers of nucleic acids, polysaccharides, phospholipids, and peptides having either $\alpha$-,$\beta$-, or $\omega$-amino acids, heteropolymers in which a known drug is covalently bound to ally of the above, polynucleotides, polyurethanes, polyesters, polycarbonates, polyureas, polyamides, polyethyleneimines, polyarylene sulfides, polysiloxanes, polyimides, polyacetates, or other polymers which will be apparent upon review of this disclosure. Such polymers are "diverse" when polymers having different monomer sequences are formed at different predefined regions of a substrate. Methods of cyclization and polymer reversal of polymers which may be used in conjunction with the present invention are disclosed in application Ser. No. 796,727, filed Nov. 22, 1991 entitled "POLYMER REVERSAL ON SOLID SURFACES," now U.S. Pat. No. 5,242,974 incorporated herein by reference for all purposes. The "position" of a monomer in a polymer refers to the distance, by number of monomers, from a terminus or other reference location on a polymer.

Peptide: A polymer in which the monomers are alpha amino acids and which are joined together through amide bonds, alternatively referred to as a polypeptide. In the context of this specification it should be appreciated that the amino acids may be the L-optical isomer or the D-optical isomer. Peptides are often two or more amino acid monomers long, and often more than 20 amino acid monomers long. Standard abbreviations for amino acids are used (e.g., P for proline). These abbreviations are included in Stryer, *Biochemistry*, Third Ed., 1988, which is incorporated herein by reference for all purposes.

Receptor: A molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex.

Specific examples of receptors which can be investigated by this invention include but are not restricted to:

a) Microorganism receptors: Determination of ligands which bind to receptors, such as specific transport proteins or enzymes essential to survival of microorganisms, is useful in a new class of antibiotics. Of particular value would be antibiotics against opportunistic fungi, protozoa, and those bacteria resistant to the antibiotics in current use.

b) Enzymes: For instance, the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the development of vaccines of which the immunogen is based on one or more of such sequences or load to the development of related diagnostic agents or compounds useful in therapeutic treatments such as for autoimmune diseases (e.g., by blocking the binding of the "self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: For instance, the receptors for insulin and growth hormone. Determination of the ligands which bind with high affinity to a receptor is useful in the development of, for example, an oral replacement of the daily injections which diabetics must take to relieve the symptoms of diabetes, and in the other case, a replacement for the scarce human growth hormone which can only be obtained from cadavers or by recombinant DNA technology. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

Substrate or Solid Support: A material having a surface and which is substantially insoluble in a solution used for coupling of monomers to a growing polymer chain. Such materials will preferably take the form of small beads, pellets, disks or other convenient forms, although other forms may be used. A roughly spherical or ovoid shape is preferred.

Basis Set: A group of monomers that is selected for attachment to a solid substrate directly or indirectly in a given coupling step. Different basis sets or the same basis sets may be used from one coupling step to another in a single synthesis.

Synthetic: Produced by in vitro chemical or enzymatic synthesis. The synthetic libraries of the present invention may be contrasted with those in viral or plasmid vectors, for instance, which may be propagated in bacterial, yeast, or other living hosts.

Symbols $x_i$ denotes the set of monomer units in reaction round i.

$x_{ij}$ denotes the j'th monomer unit in reaction round i; $x_{ij}$ can be a null ($\emptyset$)

$S_i$ refers to the separated products after reaction round i.

$P_i$ refers to the pooled products of round i and all preceding rounds.

$X_{ip}$ denotes the pooling of reactants of round i only

Reaction Graphs

A filled circle ● denotes a reaction product terminating in a particular monomer unit $x_{ij}$. The set of reaction products terminating in $x_i$ is shown by a set of circles on the same horizontal level.

Filled circles that react with each other are connected by straight lines. Pooling is shown by lines meeting below in an open circle.

Figure 7:
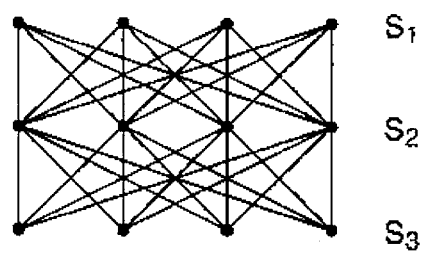
FIG. 7 illustrates a reaction graph for all 64 trinucleotides.

A factorable polynomial synthesis is one in which each monomer unit of a round is joined to each monomer of the preceding round. In a graph of such a synthesis, each filled circle at one level is connected to each filled circle of the level above. For example, the reaction graph corresponding to a three-round factorable synthesis with $$X_1=X_2=X_3=\{A,T,G,C\}$$

which yields all 64 trinucleotides, is shown in FIG. 7.

Figure 8:
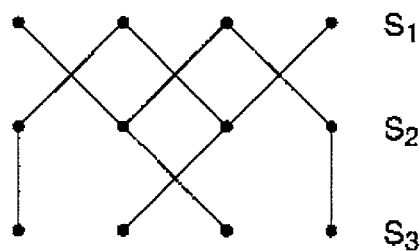
FIG. 8 illustrates the synthesis of AAT, TGC, TGT, GTA, GTG, and CCG.

In contrast, in an irreducible (prime) polynomial synthesis, at least one line in the graph of the corresponding factorable polynomial synthesis is missing. In the synthesis of AAT, TGC, TGT, GTA, GTG, and CCG only, such syntheses are illustrated in FIG. 8.

II. Overall Description

FIG. 1 is an overall illustration of one aspect of the invention. As shown therein, monomers A and B, which form all or part of a first basis set of monomers, are coupled to substrates 2 in vessels 4a and 4b. The substrates in each of the vessels 4a and 4b are divided. A portion of the substrates from each of vessels 4a and 4b are mixed in vessel 6, and divided for a subsequent coupling step into vessels 6a and 6b. Another fraction of the monomers from vessels 4a and 4b is not mixed, as indicated by vessels 10 and 12.

Thereafter, the substrates are coupled to monomers from a second basis set C,D, which may or may not be the same as the basis set A,B. As shown, the monomer C is coupled to the mixed or "pooled" substrates in vessel 6a, while the monomer D is coupled to the "pooled" substrates in vessel 6b. A portion of the products of these reactions may be mixed for later coupling steps, but at least a portion of the products in vessels 6a and 6b are not mixed.

The products in vessels 10 and 12 are preferably each divided for coupling to monomer C as shown in vessels 10b and 12b, while the substrates in vessels 10a and 12a are used to couple the monomer D to the growing polymer chain. The products of the reactions in vessels 10a and 10b are mixed or pooled, and placed in vessel 20. The products of the reactions in vessels 12a and 12b are mixed or pooled, and placed in vessel 22.

The products in vessels 20 and 22 are, thereafter, used to identify a first monomer in a polymer which is complementary to a receptor of interest. It is assumed for the sake of illustration herein that the monomer sequence AC is complementary to the receptor R. A receptor labeled with, for example, a fluorescent or radioactive label *, is exposed to the materials in vessels 20 and 22, and unbound receptor is separated from the solid supports. Binding to the substrates will occur only with the substrates in vessel 20. Fluorescence is, therefore, observed only in vessel 20. From this observation, it is possible to conclude that the first monomer in a complementary receptor is A, since all of the polymers in vessel 22 contain the first monomer B. Conversely, all of the polymers in vessel 20 contain the first monomer A.

The labeled receptor is also exposed to the polymers in vessels 26a and 26b. In this case, binding of the labelled receptor will be observed only in vessel 26a. Accordingly, it is possible to identify the second monomer in a complementary sequence as C, since none of the polymers in vessel 26b contain the second monomer C, while all of the polymers in vessel 26a contain the second monomer C. Therefore, it is possible to conclude that the sequence AC is complementary to R since binding is observed in vessels 26a and 20.

FIG. 1b illustrates aspects of a preferred embodiment of the invention in greater detail with a larger polymer chain. According to the embodiment shown in FIG. 1b, a basis set of 3 monomers, A, B, and C is used in each coupling step. The synthesized polymers are to be three monomers long. It will be recognized by those of skill in the art that the number of monomers in a basis set and the number of coupling steps will vary widely from one application to another. Also, intervening coupling steps of, for example, common monomer sequences may be used in some embodiments. Therefore, when a polymer is represented by, for example, the notation "ABC" or "ABE" herein, it is to be understood that other common monomers may be added such that ABDC and ABDE are represented by ABC and ABE. The embodiment shown in FIG. 1b is provided merely as an illustration of the invention.

As shown in FIG. 1b, the synthesis takes place on a plurality of substrates 2. According to a preferred aspect of the invention, the substrates 2 take the form of beads, such as those made of glass, resins, plastics, or the like. The term "beads" is used interchangeably herein with the word "substrate," although it is to be understood that the beads need not take on a circular or ovoid shape and can take the form of any suitable substrate. It will be further understood that the substrates 2 are shown only in the top portion of FIG. 1b, but the substrates will be present in each of the reaction products shown in FIG. 1b to the left of the monomer sequences. In each vessel in FIG. 1b, all of the possible polymer products are listed. Many "copies" of each sequence will generally be present.

According to one embodiment, conventional Merrifield techniques are used for the synthesis of peptides, such as described in Atherton et al., "Solid Phase Peptide Synthesis," IRL Press, (1989), previously incorporated herein by reference for all purposes. Of course other synthesis techniques will be suitable when different monomers are used. For example, the techniques described in Gait et al., *Oligonucleotide Synthesis*, previously incorporated by reference herein by reference for all purposes, will be used when the monomers to be added to the growing polymer chain are nucleotides. These techniques are only exemplary, and other more advanced techniques will be used in some embodiments such as those for reversed and cyclic polymer synthesis disclosed in U.S. application Ser. No. 07/796,727, now U.S. Pat. No. 4,242,974 previously incorporated herein by reference for all purposes.

A large number of beads are utilized such that the beads may be separated into separate reaction vessels in later steps and still be present in sufficient numbers such that the presence of a complementary receptor may be detected. As a general rule, it will be desired to use 10 to 100 or more times the number of combinatorial possibilities for the synthesis so as to ensure each member of each set is synthesized. Also, the use of a large number of beads ensures that pooled reaction products are distributed to each succeeding reaction vessel when a pooled group of beads is divided.

The beads are preferably as small as possible so that the reaction vessels and other material handling equipment utilized in the process may also be as small as possible. Preferably, the beads have a diameter of less than about 1 mm, and preferably less than about 100 μm, and more preferably less than about 10 μm. In some embodiments, the synthesis is carried out in solution.

As shown in FIG. 1b the monomers A, B, and C are coupled to substrates in three reaction vessels 4a, 4b, and 4c, respectively. A single substrate is shown in FIG. 1b for purposes of clarity, but it will be recognized that in each reaction vessel a large number of beads will be present. Accordingly, a large number of "copies" of the substrates with the respective monomers coupled thereto are formed in each of reaction vessels 4a, 4b, and 4c. It will be recognized that the monomers need not be directly coupled to the substrate, and in most cases linker molecules will be provided between the monomers and the substrate, such as those described in U.S. application Ser. No. 07/624,120, incorporated herein by reference for all purposes. Also, it should be recognized that the steps shown in FIG. 1b may be preceded by or followed by other synthesis steps which may or may not be combinatorial steps using the techniques described herein.

Thereafter, a fraction of the products in each of vessels 4a, 4b, and 4c are combined, mixed, and redistributed to each of reaction vessels 6a, 6b, and 6c. The remaining fraction of the products in each of vessels 4a, 4b, and 4c is not combined. Instead, the remaining fraction of the products in reaction vessel 4a is divided and placed in reaction vessels 8a, 8b, and 8c. Similarly, the remaining fraction of the products in vessel 4b is divided and placed in vessels 10a, 10b, and 10c. The remaining fraction of the products in reactant vessel 4c is divided and placed in reaction vessels 12a, 12b, and 12c.

The reactants placed in vessels 6a, 6b, and 6c are referred to herein as "pooled" reactants since they comprise a mixture of the products resulting from the previous coupling step. The reactants placed in vessels 8, 10, and 12 by contrast are separate reactants since they are not mixtures of the products from the previous coupling steps. According to a preferred embodiment of the invention, after the reactants in vessels 8, 10, and 12 are subjected to a separate coupling step, they are subjected only to pooled coupling steps thereafter. Conversely, in each subsequent coupling step, the pooled reactants are subjected to a coupling step, and divided for subsequent separate and pooled coupling steps.

Preferably, the reactants are divided such that a greater fraction of the beads is distributed for pooled synthesis. For example, in FIG. 9, 4/5 of the beads would go to the first pooled group 905 while 1/5 would go to the unpooled group 903.

Thereafter the monomers A, B, and C are coupled to the growing polymer chain in reaction vessels 8a, 8b, and 8c, respectively. The resulting polymers then have the monomer sequence CA, CB, and CC in reaction vessels 8a, 8b, and 8c, respectively. The products of these reactions are then mixed or pooled in reaction vessel 9, and the mixture is again divided among reaction vessels 14a, 14b, and 14c. The monomers A, B, and C are again coupled to the growing polymer chains in vessels 14a, 14b, and 14c, respectively. The products of these reactions are again mixed or pooled and placed in vessel 16a.

Similarly, the monomers A, B, and C are coupled to the growing polymer chain in reaction vessels 10a, 10b, and 10c, then mixed in vessel 18, divided, and placed in reaction vessels 20a, 20b, and 20c. Monomers A, B, and C are coupled to the growing polymer chain in vessels 20a, 20b, and 20c respectively, mixed, and placed in vessel 16b. Monomers A, B, and C are also coupled to the growing polymer chain in reactant vessels 12a, 12b, and 12c respectively, mixed, and placed in vessel 21. These products are divided for reaction with monomers A, B, and C in vessels 22a, 22b, and 22c respectively, mixed, and placed in vessel 16c. A characteristic feature of the preferred embodiments of the present invention should be noted in the right half of FIG. 1b. Specifically, once the products of a reaction are not pooled (such as in vessels 8, 10, and 12), the products of coupling steps are always pooled thereafter.

Referring to the left hand portion of FIG. 1b, the pooled reactants in vessels 6a, 6b, and 6c are coupled to monomers A, B, and C respectively, resulting in the products shown in vessels 26a, 26b, and 26c. Since the products in vessels 26a, 26b, and 26c are derived from a "chain" of pooled reactions, the products are separated for both pooled and separate reactions. Specifically, a portion of the substrates in vessels 26a, 26b, and 26c are combined, mixed, and divided for pooled reactions with monomers A, B, and C in vessels 28a, 28b, and 28c respectively. In addition, the remaining portion of the products in vessels 26a, b, and c are separately divided and placed in reaction vessels 30a–c, 32a–c, and 34a–c respectively. The materials in vessels 30a, 32a, and 34a are coupled to monomer A, the materials in vessels 30b, 32b, and 34b are coupled to monomer B, and the materials in vessels 30c, 32c, and 34c are coupled to monomer C. Since the products in vessels 30, 32, and 34 result have been preceded by a separate reaction, the products in vessels 30, 32, and 34 are pooled, or mixed, and placed in vessels 36a, 36b, and 36c, respectively.

For reasons that will be discussed further below, the vessels in group 42 are used to determine the identity of the monomer in the first position in a polymer that is complementary to a receptor. The vessels in group 44 are used to determine the identity of the second monomer in a polymer that is complementary to a receptor. The vessels in group 46 are used to determine the identity of the third monomer in a polymer that is complementary to a receptor.

For example, assume that a given receptor is complementary to the monomer sequence ABC, but the sequence of the complementary polymer is not known ab initio. If the receptor is labelled with an appropriate label such as fluorescein and placed in each of the vessels in groups 42, 44, and 46, fluorescence will be detected only in vessels 16c, 36b, and 28c since the polymer sequence ABC appears only in these vessels. Fluorescence may be detected using, for example, the methods described in Mathies et al., U.S. Pat. No. 4,979,824, incorporated herein in its entirety by reference for all purposes.

Since all of the polymers in vessel 16c have monomer A in the first position, and none of the polymers in vessels 16a or 16b have monomer A in the first position, it is readily determined that the monomer in the first position of a complementary polymer is the monomer A. Similarly, since all of the polymers in vessel 36b have the monomer B in the second position, it is readily determined that the monomer B must occupy the second position of a complementary polymer sequence. Similarly, since all of the polymers in vessel 28c have a C monomer in the third position, the complementary receptor must have a C in its third position. Therefore, it would readily be determined that the complementary sequence to the receptor has the monomer sequence ABC.

As will be seen upon careful examination of the sequences in the vessel groups 42, 44, 46, ambiguities will generally not arise, regardless of the monomer sequence which is complementary to the receptor of interest. As a point of comparison, if the receptor of interest is complementary to the sequence BBA, fluorescence would be detected only in vessels 16b, 36b, and 28a. From this information is becomes clear that the complementary monomer sequence must be BBA.

The above embodiment illustrates the synthesis of pooled groups of polymers by way of separation into separate vessels, followed by coupling and mixing. It will be recognized that this is only for convenience of illustration and that in some embodiments the pooled groups of polymers will be synthesized under controlled conditions by simultaneous reaction of each of the monomers to be coupled to the polymers in a single reactor. Further, it will be recognized that the synthesis steps above will be supplemented in many embodiments by prior, intermediate, and subsequent coupling steps, which are not illustrated for ease of illustration.

The above method may be generally illustrated by way of the adoption of appropriate nomenclature. For example let $X_i$ denote the set of monomer units that become joined to a growing chain at reaction round i. For example, suppose that $$X_1=\{L,G\} X_2=\{P,Y\} X_3=\{R,A\}$$

A particular monomer is denoted by $x_{ii}$. For example, $$x_{3,1}=R$$

The reaction products $S_3$ of such a three-round peptide synthesis is concisely represented by $$S_3=X_3X_2X_1$$

$S_3$ is determined by expanding a reaction polynomial as described in Fodor et al., *Science* (1991) 251:767–773, incorporated herein by reference for all purposes.

$$S_3=(R+A)(P+Y)(L+G)$$

and so $S_3$ consists of 8 tripeptides:

RPL, RYL, RPG, RYG, APL, AYL, APG, and AYG
$S_{ij}$ denotes a set of reaction products terminating in monomer unit $x_{ij}$. In the above synthesis, for example, $$S_{12}=G \ S_{21}=\{PL,PG\} S_{32}=\{APL,AYL,APG,AYG\}$$

Figure 2:
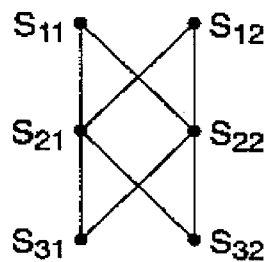
FIG. 2 illustrates a simple reaction graph.

This three-round synthesis can also be represented by a reaction graph, as shown in FIG. 2. Each reaction product of round i is depicted by a filled dot on the same horizontal level. Each dot of round i is joined to each dot of the preceding round and to each dot of the succeeding round. For example, the dot denoting $S_{21}$ is joined to the dots for $S_{11}$ and $S_{12}$, and also to the dots $S_{31}$ and $S_{32}$. Note that dots on a level are never connected to each other because, by definition, monomer units of a round do not combine with one another.

It is generally assumed that the products of each round are spatially separate and addressable. Each can then be readily assayed. However, the number of compounds generated by a combinatorial synthesis can, after a few rounds, greatly exceed the number of experimentally available bins or vessels. It is then advantageous to pool the products of one or more rounds of synthesis. For example, a five-round synthesis using the basic set of 20 amino acids yields $20^5$ or $3.2\times10^6$ pentapeptides. In contrast, if the products of the first two rounds are pooled, the subsequent three rounds yield only 8,000 sets of products. Information is lost in the pooling process, but the number of products becomes experimentally tractable.

The above representation of combinatorial synthesis may be modified to take into account the effect of pooling.

Figure 3:
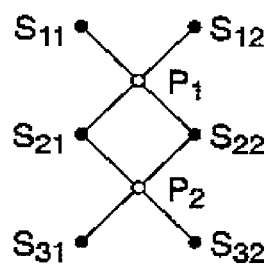
FIG. 3 illustrates a reaction graph with pooled and separate products.

Suppose that products of the first two rounds of the three-round synthesis mentioned earlier are pooled. The reaction graph for a with pooled steps is shown in FIG. 3. The pooled products of round i are denoted by $P_i$ to distinguish them for the separate products $S_i$. In a reaction graph, pooling is shown by the convergence of lines from the $S_i$ that are pooled. $P_i$ is then shown as an open circle.

In this example, $$P_1=\{L+G\} P_2=\{PL+PG+YL+YG\}$$

$$S_3=X_3P_2=\{RPL+RPG+RYL+RYG,APL+APG+AYL+AYG\}$$

The plus sign joins products that are present in a mixture. In contrast, products separated by commas are located in separate bins and are spatially addressable. In this example, the pooled products of the second round are located in one bin, whereas the products after three rounds are located in two bins. One bin contains the mixture RPL+RPG+RYL+RYG, and the other bin contains the mixture APL+APG+AYL+AYG.

Figure 4:
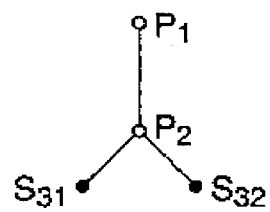
FIG. 4 illustrates a simplified reaction graph.

This reaction graph can be simplified. Suppose that $P_1$ was coupled to a equimolar mixture of $X_{21}$ and $X_{22}$ in a single bin. If the coupling efficiencies for all species are the same, the amounts and kinds of products obtained would be the same as that given by coupling $P_1$ with $X_{21}$ and $X_{22}$ in separate bins and then pooling the products. Thus, pooled products and pooled reactants are formally equivalent provided that the reactions occur in a substantially homogeneous solution and all coupling efficiencies are substantially the same. Hence, an $X_3P_2$ synthesis can be most simply represented by the reaction graph shown in FIG. 4.

The line joining $P_2$ to $P_1$ means that all products in $P_1$ are coupled equally to all reactants $X_2$, either by (1) adjusting the concentrations of reactants or (2) driving the reactions to completion in separate bins, followed by pooling. For beads or other discrete particles, (2) more often applies so that each particle expresses only one kind of product.

By way of comparison, the synthesis of 180 pentapeptides in Furka et al., "General Method for Rapid Synthesis of Multicomponent Peptide Mixtures," *Int. J. Peptide Protein Res.* (1991) 37:487–493, is represented with the above nomenclature as $S_5=X_5P_4$, where $X_1=\{A\}$, $X_2=\{E,F,K,\}$, $X_3=\{E,P,K\}$, $X_4=\{E,F,G,K\}$, and $X_5=\{E,G,K,L,P\}$. The peptide combinatorial library synthesis in Houghten et al., "Generation and Use of Synthetic Peptide Combinatorial Libraries for Basic Research and Drug Discovery," *Nature* (1991) 354:84–86 is $S_6=X_6X_5P_4$, where each $X_i$ is a set of 18 naturally occurring amino acids. The $S_6$ products are located in 18×18 or 324 bins, each containing a mixture of $18^3$=5,832 hexapeptides. The pooled synthesis in Lam et al., "A new type of synthetic peptide library for identifying ligand-binding activity," *Nature* (1991) 354:82–84, is represented using the above nomenclature as $P_5$, where each $X_i$ is a set of 19 naturally-occurring amino acids. $P_5$ is a mixture of $19^5$=2.48×10$^6$ beads, each bearing one kind of peptide.

In the pooled syntheses of Houghten, Lam, and Furka, all products from round 1 to round n are mixed. In Furka's synthesis ($X_5,P_4$), the first four rounds are pooled. In an $X_3P_2$ synthesis, the first two rounds are pooled.

Figure 5A:
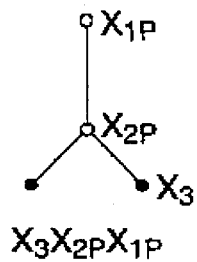
FIGS. 5a, 5b, and 5c illustrate a family of pooled syntheses.
Figure 5B:
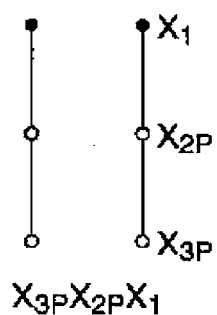
Figure 5C:
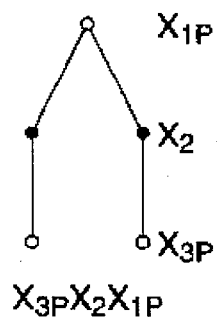
Figure 6:
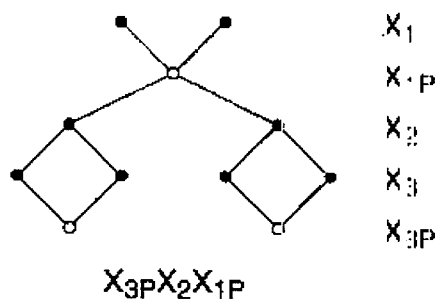
FIG. 6 illustrates a reaction graph for forming the products $X_3X_2X_{1p}$.

Representative pooled syntheses techniques according to one preferred embodiment of the invention herein are shown in FIGS. 5a, 5b, and 5c. The symbol $X_{ip}$ means that the reactants of round i have been pooled without pooling the reaction products of previous rounds. This is achieved by, for example, (1) mixing the reactants $X_i$ or (2) by reacting each member of $X_i$ with each reaction product of $S_{i-1}$, as shown in FIG. 6 for $X_{3p}X_2X_{1p}$.

For pentapeptides made of the naturally occurring 20 amino acids for example, a family of five pooled syntheses groups according to the invention herein will be particularly useful:

$$X_5X_{4p}X_{3p}X_{2p}X_{1p} \quad X_{5p}X_4X_{3p}X_{2p}X_{1p} \quad X_{5p}X_{4p}X_3X_{2p}X_{1p}$$
$$X_{5p}X_{4p}X_{3p}X_2X_{1p} \quad X_{5p}X_{4p}X_{3p}X_{2p}X_1$$

The products of each of these five syntheses product groups would be located in 20 physically isolated bins. Each bin would contain a different mixture of 160,000 pentapeptides. As with the trimer illustrated in FIG. 1b, the identity of the monomers forming a complementary pentamer would be determined unambiguously by identifying which of the 20 bins in each of the five syntheses product groups showed binding to a receptor.

It is to be recognized that while "bins" are referred to herein for the sake of simplicity, any of a variety of techniques may be used for physically separating the peptide or other polymer mixtures.

More specifically, a sequence of monomers in a complementary ligand for a receptor is identified as follows. For example, consider the family of pooled tripeptide libraries made of the 20 naturally occurring amino acids:

$$X_3X_{2p}X_{1p} \quad X_{3p}X_2X_{1p} \quad X_{3p}X_{2p}X_1$$

The most potent amino acid at the left position $(x_{3i})$ is revealed by analysis of the 20 bins of $X_3X_{2p}X_{1p}$; $x_{2j}$ is determined by analysis of $X_{3p}X_2X_{1p}$; and $x_{1k}$ is determined by analysis of $X_{3p}X_{2p}X_1$. The sequence of the most potent tripeptide is then predicted to be $x_{3i}x_{2j}x_{1k}$. Accordingly, each pooled group in the library reveals the identity of a monomer in a different position in a complementary polymer.

It will be recognized that it will not always be desirable to determine the identity of the entire sequence of monomers in a polymer that is complementary to a receptor. Instead, it will only be necessary to determine the identity of selected monomers in a polymer in some instances. The monomers of interest may be at intermediate locations on the chain of polymer, and may be interspersed by other monomers. Accordingly, in a more general sense, the method herein provides for the synthesis of a library of polymers. The library is used to identify at least two monomers of interest in the polymer chain.

For example, the identity of the $x_{2j}$ monomer is determined by analysis of a library of polymers T—$X_2$—I—$X_{1p}$—T; and the identity of the monomer $x_{1k}$ is determined by analysis of a library of polymers T—$X_{2p}$—I—$X_1$—T, where T indicates terminal groups on the polymer chain, which may be null groups, and I designates intermediate groups in the polymer chain, which may also be null groups.

The method of making the library used pooled and separate synthesis steps. The polymers have at least two monomer locations at which it is desired to determine the identity of monomers which provide a polymer with a sequence complementary to a receptor. The library is synthesized such that the products of a pooled synthesis are separated and subjected to a separate synthesis and a second pooled synthesis. The products of the separate synthesis are subjected to a series of pooled syntheses, without any further separate synthesis in preferred embodiments. Conversely, the products of the second pooled synthesis are divided and subjected to both a separate syntheses and a third pooled synthesis.

The synthesis steps result in a library of polymers having at least first and second subsets. The first subset is used to determine the identity of a monomer or monomers at a first location in the polymer chain which is complementary to a receptor. The second subset of the library is used to determine the identity of a monomer or monomers at a second location in the polymer chain which is complementary to a receptor.

The method uses summated assays to identify optimal sequences. The distribution of activities in the mixture assayed remains unknown. Only the aggregate activity is determined. More information can be obtained from analyses of beads or other particles that contain multiple copies of one kind of sequence. The activity of each bead can be quantitated even though its identity is unknown.

Suppose that 2 μm diameter beads are used for pooled syntheses. Some pertinent properties of typical beads are:

Volume=4.2 μm$^3$

Surface area=12.6 μm$^2$

Number of target sites=$1.3 \times 10^5$ (assuming 1 per 100 mm$^2$)

Number of beads per cm$^3$=$2.4 \times 10^{11}$

Fluorescence measurements of beads flowing rapidly through a laser beam are made using techniques such as those in U.S. Pat. No. 4,979,824, previously incorporated herein by reference for all purposes, which provide exemplary methods for determining the distribution of activities in a pooled synthesis.

Assume a light beam diameter of 2 μm is used for detection of fluorescein labeled beads, at a flow rate of 20 cm/s. The transit time of a bead through the beam is then 10 μs. The emission rate from a single chromophore can be as high as $10^8 s^{-1}$. If 10% of the target sites are occupied, this corresponds to an emission rate of about $10^{12} s^{-1}$, or $10^7$ emitted photons in 10 μs, which would be easily detected. If 10% of the sample volume is occupied by beads, an average of one bead would pass through the beam every 0.1 ms. Thus, $10^4$ beads could be analyzed per second. A library of $3.2 \times 10^6$ beads (each bearing a different pentapeptide) could be analyzed in about 6 minutes.

Alternatively, the beads may be analyzed by spreading them on a surface. For example, $3.2 \times 10^6$ beads would occupy $1.28 \times 10^7$ μm$^2$ if packed together in a square array. In 1.28 cm$^2$, these beads would occupy 10% of the surface area. Smaller beads, say 0.2 μm$^2$, would give a sufficient fluorescence signal. The advantage of smaller beads is that higher bead densities could be used, leading to a marked reduction in the time needed for analysis.

The fluorescence pulse height distribution emerging from either analysis would reveal whether there are many or few optimal sequences contained within the sample of beads. In the simplest case, a single bright bead is seen in just one bin of a pooled synthesis. The identity of the best sequence then comes directly from analysis of each pooled synthesis of the family.

In other cases, there is a distribution of intensities within several sets of beads. As a general rule, positioned libraries where binding is exhibited in multiple bins indicates that a particular position plays a less significant role in binding. In some embodiments, positions where ambiguity are detected are further evaluated through use of the VLSIPS™ technique. The VLSIPS™ arrays will vary only those positions wherein the monomer has not been determined unambiguously. The present invention is used, therefore, to reduce the number of polymers which will be screened with VLSIPS™ in some embodiments. To synthesize the VLSIPS™ array, one will utilize a substrate "S" with a surface. Linker molecules "L" are optionally provided on a surface of the substrate. The purpose of the linker molecules, in some embodiments, is to facilitate receptor recognition of the synthesized polymers.

On the substrate or a distal end of the linker molecules, a functional group with a protective group $P_0$ is provided. The protective group $P_0$ may be removed upon exposure to radiation, electric fields, electric currents, or other activators to expose the functional group.

In a preferred embodiment, the radiation is ultraviolet (UV), infrared (IR), or visible light. As more fully described below, the protective group may alternatively be an electrochemically-sensitive group which may be removed in the presence of an electric field. In still further alternative embodiments, ion beams, electron beams, or the like may be used for deprotection.

Concurrently or after exposure of a known region of the substrate to light, the surface is contacted with a first monomer unit $A_1$ which reacts with the functional group which has been exposed by the deprotection step. The first monomer includes a protective group $P_1$. $P_1$ may or may not be the same as $P_0$.

Accordingly, after a first cycle, known first regions of the surface may comprise the sequence:

while remaining regions of the surface comprise the sequence:

Thereafter, second regions of the surface (which may include the first region) are exposed to light and contacted with a second monomer $B_2$ (which may or may not be the same as $A_1$) having a protective group $P_2$. $P_2$ may or may not be the same as $P_0$ and $P_1$. After this second cycle, different regions of the substrate may comprise one or more of the following sequences:

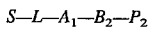

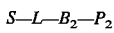

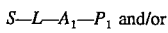 and/or

The above process is repeated until the substrate includes desired polymers of desired lengths. By controlling the locations of the substrate exposed to light and the reagents exposed to the substrate following exposure, the location of each sequence will be known.

Thereafter, the protective groups are removed from some or all of the substrate. The process results in a substrate having a surface with a plurality of polymers of the following general formula:

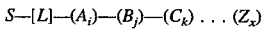

where square brackets indicate optional groups, and $A_i \ldots Z_x$ indicates any sequence of monomers.

Figure 9:
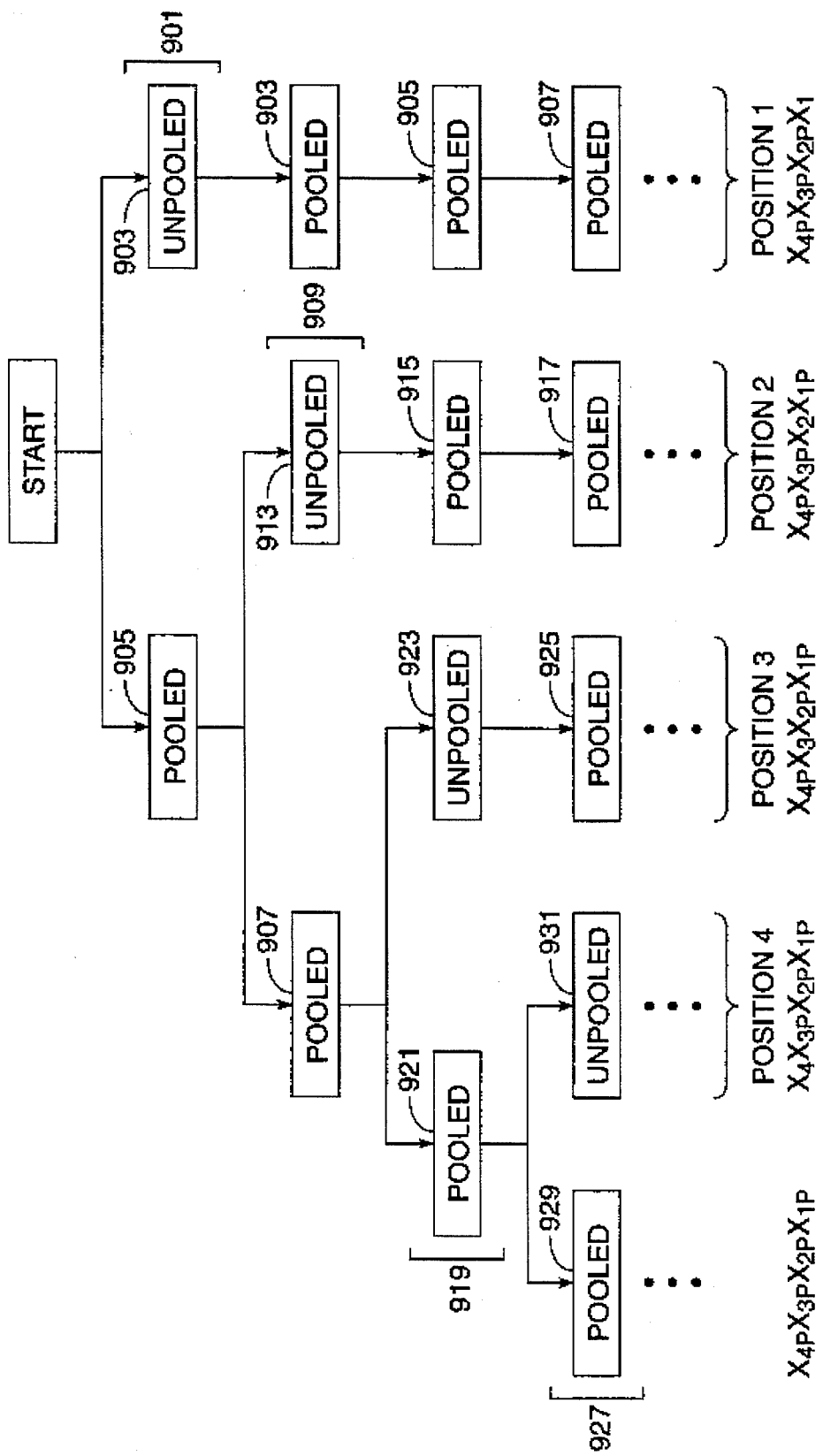
FIG. 9 provides an alternative representation of the invention.

FIG. 9 provides an alternative description of the invention. As shown therein, at step 901 a collection of substrates is subjected to pooled and separate coupling steps, resulting in pooled and separate products 905 and 903, respectively. Products 903 are analogous to the products shown in vessels 8, 10, and 12, and products 905 are analogous to the products in vessel 6. The collection of substrate products 903 are then subjected to pooled coupling steps 903, 905, 907, and 909, i.e., the subsequent coupling steps to the separate reactants are only pooled coupling steps. Accordingly, the identity of the monomer in the first position of a polymer complementary to a receptor is determined by evaluation of the products 907.

Conversely, the pooled products 905 are divided and subjected to pooled and separate coupling steps 909, resulting in pooled and separate products 907 and 913, respectively. As with the separate products 903, the separate products 913 are subjected only to pooled coupling steps thereafter, resulting in pooled products 915 and 917. The products 917 are used to determine the monomer in a second position in a polymer complementary to a receptor of interest.

In the same manner, the pooled products 907 are divided and subjected to pooled and separate coupling steps 919, resulting in pooled and separate products 923 and 921. The separate products 923 are subjected only to a pooled reaction thereafter, the products 925 being used to determine the monomer in a third position in a polymer complementary to a receptor of interest. The pooled products 921 are divided and subjected to pooled and separate reactions 927, resulting in pooled and separate products 929 and 931. The products 907, 917, 925, 931, and 929 are used to identify complementary receptors. In the preferred embodiment, the pooled products 927 are first used to determine if any polymers of interest are present. The separate products 931 are used to determine the identity of a monomer in a fourth position of a polymer complementary to a receptor.

As shown in FIG. 9, pooled products that have not been subjected to prior separate reactions are divided and subjected to pooled and separate reactions according to the invention herein. Conversely, products which result from a prior separate coupling step are only subjected to pooled coupling steps.

Figure 10:
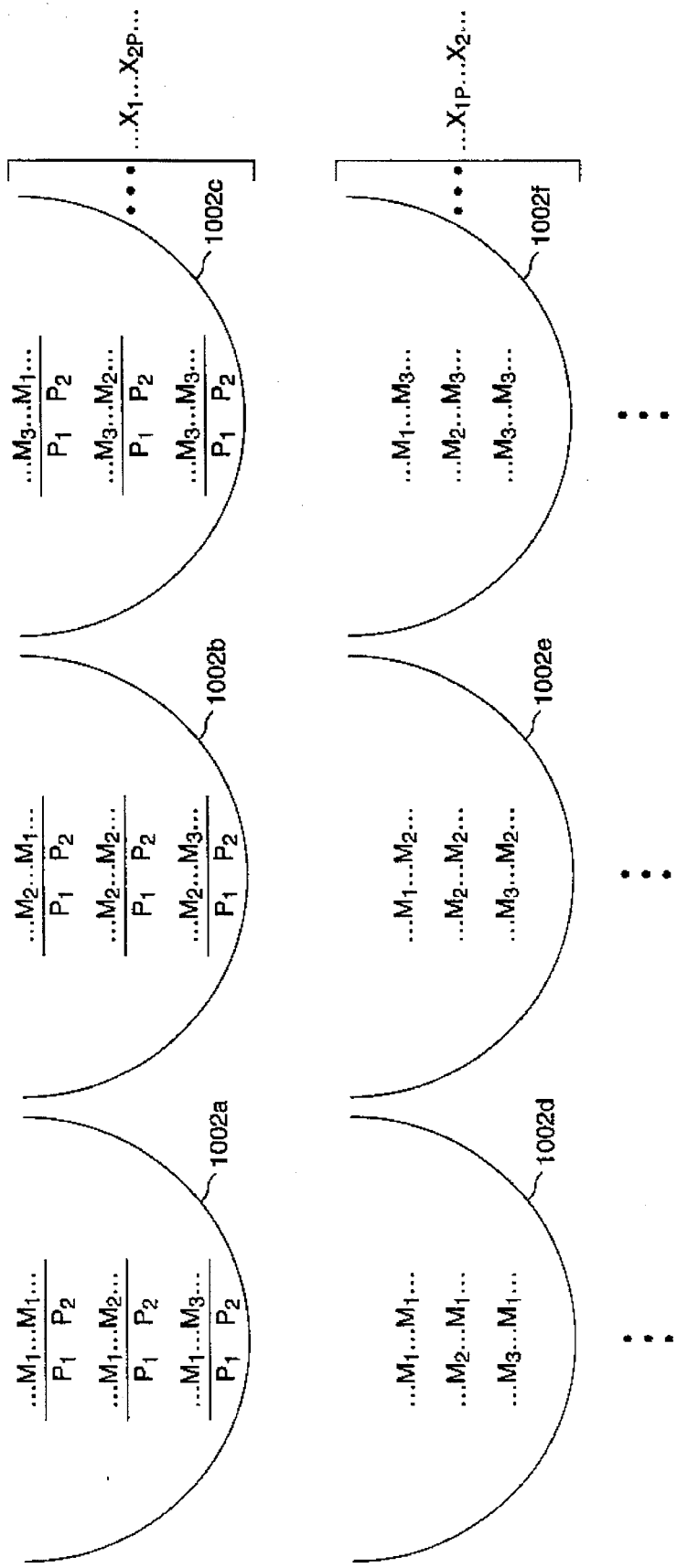
FIG. 10 illustrates a polymer library according to one embodiment of the invention.

FIG. 10 illustrates a library of polymers which will be useful in accordance with the invention herein. As shown therein, the polymers have a number of monomer positions, designated by $p_i$. The monomers have at least two positions of interest, $p_1$ and $p_2$. $p_1$ and $p_2$ may in some embodiments be separated by various intermediate monomers or groups, and may also have various terminal groups attached thereto. The monomers are placed in a number of physically isolated bins or vessels 1002. The bins or vessels 1002 may in fact be attached, such as in a microtiter plate, or the bins/vessels may be distinct containers such as test tubes, microtiter trays, or the like.

A first bin 1002a contains polymers with a first monomer $M_1$ in the first position $p_1$ in each of the polymers therein. However, the polymer molecules in the first bin have a variety of different monomers such as $M_1$, $M_2$, and $M_3$ in a second position $p_2$. In the second bin 1002b a second monomer $M_2$ is in the first position $p_1$ in each of the polymers therein, while different monomers such as $M_1$, $M_2$, and $M_3$ are in the second position $p_2$. In the third bin 1002c a third monomer $M_3$ is in the first position $p_1$ in each of the polymers therein, while different monomers such as $M_1$, $M_2$, and $M_3$ are in the second position $p_2$. The first, second, and third bins comprise all or part of a collection of bins $\ldots X_1 \ldots X_{2p} \ldots$ Conversely, fourth bin 1002d contains polymers with a first monomer $M_1$ in the second position $p_2$ in each of the polymer molecules therein. The polymer molecules in the first bin have a variety of different monomers such as $M_1$, $M_2$, and $M_3$ in their first position $p_1$. In the fifth bin 1002e a second monomer $M_2$ is in the second position $p_2$ in each of the polymers therein, while different monomers such as $M_1$, $M_2$, and $M_3$ are in the first position $p_1$. In the sixth bin 1002f a third monomer $M_3$ is in the second position $p_2$ in each of the polymers therein, while different monomers such as $M_1$, $M_2$, and $M_3$ are in the first position $p_1$. The fourth, fifth, and sixth bins comprise all or part of a collection of bins $\ldots X_{1p} \ldots X_2 \ldots$ In screening studies, the bins 1002a, 1002b, and 1002c are used to determine the identity of the monomer in position 1 of a polymer that is complementary to a receptor of interest. The bins 1002d, 1002e, and 1002f are used to determine the identity of the monomer in position 2 of a polymer that is complementary to a receptor of interest.

It will be recognized that the polymers which are screened according to the above methods can be of widely varying length and composition. For example, in preferred embodiments, the polymer molecules are preferably greater than 3 monomer units long, preferably greater than 5 monomer units long, more preferably greater than 10 monomer units long, and more preferably more than 20 monomer units long. Although a simplified library is shown in FIG. 10, it will be recognized that in most embodiments, the library will include additional polymer bins so as to identify the monomers at more than 3 positions, preferably more than 5 positions, more preferably more than 10 positions, and more preferably more than 20 positions in a complementary polymer to a receptor.

III. Polynomial Factoring Applied to Screening

In some embodiments a population of all possible polymers of length n are synthesized. If a receptor is found to bind with one of the polymers in the mixture, a second synthesis is conducted in which the polymers are "factored," i.e., two bins are formed, each having half of the population synthesized initially. It is then determined which of the two bins shows binding to the receptor, the bin which exhibits binding being referred to as a "target group." Yet another synthesis is conducted in which two bins are created, each with half of the population of the target group in the earlier bin. The process is repeated until the sequence of the polymer or polymers that show binding to the receptors is determined.

More specifically, the invention provides for the synthesis of a population:

$$P = \sum_{i=1}^{n} X_i \sum_{j=1}^{n} X_j$$

This solution is factored as:

$$P = \sum_i X_i \left[ \sum_j^{n/2} X_j + \sum_{n/2}^{n} X_j \right] = P_1 + P_2$$

where:

$$P_1 = \sum_{i=1}^{n} X_i \sum_{j=1}^{n/2} X_j; \text{ and}$$

$$P_2 = \sum_{i=1}^{n} X_i \sum_{n/2}^{n} X_j$$

If $P_1$ generates a "hit," $P_1$ is factored. If $P_2$ generates a "hit," $P_2$ is factored. Each synthesis requires only half the number of polymers made in the prior step.

IV. Conclusion

The above description is illustrative and not restrictive. Many variations of the invention will become apparent to those of skill in the art upon review of this disclosure. Merely by way of example while the invention is illustrated primarily with regard to the synthesis of oligonucleotides and peptides, the invention will also find utility in conjunction with the synthesis and analysis of a wide variety of additional polymers. The scope of the invention should, therefore, be determined not with reference to the above description, but instead should be determined with reference to the appended claims along with their full scope of equivalents.

---

---

What is claimed is:

1. A method of identifying first and second monomers in a polymer that specifically binds to a receptor of interest, said polymer selected from the group consisting of oligonucleotides and peptides, comprising the steps of:

coupling first and second monomers in a first basis set to individual solid substrates and mixing substrates to form first pooled products;

coupling said first and second monomers from said first basis set to individual substrates, and not mixing said substrates to form at least first and second separate products;

separately coupling first and second monomers from a second basis set to substrates from said first pooled products and not mixing said substrates to form at least third and fourth separate products;

coupling said first and second monomers from said second basis set to individual substrates from said first separate products and mixing said substrates to form second pooled products;

coupling said first and second monomers from said second basis set to individual substrates from said second separate products to form third pooled products; and exposing a receptor to said third and fourth separate products to identify a second monomer in a polymer which is complementary to a receptor, and exposing said second and third pooled products to said receptor to identify a first monomer in a polymer which specifically binds to said receptor.

2. The method as recited in claim 1 wherein said step of exposing to a receptor is preceded by the step of performing additional steps of coupling and mixing to said second pooled products and said third pooled products.

3. The method as recited in claim 1 further comprising the step of mixing a portion of said third and fourth separate products to form fourth pooled products.

4. The method as recited in claim 3 further comprising the step of separately coupling monomers from a third basis set to said fourth pooled products.

5. The method as recited in claim 1 wherein said monomers are amino acids.

6. The method as recited in claim 1 wherein said monomers are nucleotides.

7. The method as recited in claim 1 wherein said steps are repeated to screen polymers having at least three monomers therein.

8. The method as recited in claim 1 wherein at least one of said first and second monomers cannot be determined unambiguously, further comprising the steps of:

synthesizing an array of potentially specifically binding polymers using a light-directed synthesis technique; and detecting binding of said receptor to said potentially specifically binding polymers.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp  Val  Pro  Asp  Tyr  Ala
    1                       5